United States Patent [19] [11] 4,365,991
de Silva [45] Dec. 28, 1982

[54] PROPIONIC ACID OXIMES

[75] Inventor: Wijitha de Silva, Schöfflisdorf, Switzerland

[73] Assignee: Hoffmann-La Roche Inc., Nutley, N.J.

[21] Appl. No.: 241,189

[22] Filed: Mar. 6, 1981

[30] Foreign Application Priority Data

Mar. 10, 1980 [CH] Switzerland .......................... 1861/80
Jan. 8, 1981 [CH] Switzerland ............................ 88/81

[51] Int. Cl.³ ..................... A01N 39/02; C07C 131/00
[52] U.S. Cl. ........................................ 71/121; 564/254; 560/21; 560/62; 562/435; 562/472
[58] Field of Search ........................... 564/254; 71/121

[56] References Cited

U.S. PATENT DOCUMENTS 3,592,920 7/1971 Gutman et al. ..................... 564/254
4,200,587 4/1980 Suchy ................................. 564/254

Primary Examiner—Natalie Trousof
Assistant Examiner—L. Hendriksen
Attorney, Agent, or Firm—Jon S. Saxe; George M. Gould; John B. Wilson

[57] ABSTRACT

Propionic acid oximes of the general formula

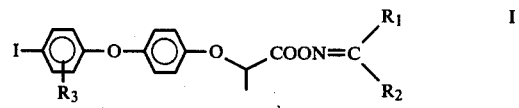

wherein $R_1$ is hydrogen, alkyl of from 1 to 6 carbon atoms or cycloalkyl of from 3 to 6 carbon atoms, $R_2$ is hydrogen, alkyl of from 1 to 6 carbon atoms, alkenyl of from 2 to 6 carbon atoms or alkynyl of from 2 to 6 carbon atoms, or $R_1$ and $R_2$ together with the carbon atom to which they are attached form a cyclopentane or cyclohexane ring which can be mono-, di- or trisubstituted with alkyl of from 1 to 3 carbon atoms, $R_3$ is hydrogen, halogen or nitro with the proviso that $R_1$ and $R_2$ are not simultaneously hydrogen, processes for their manufacture, herbicidal compositions containing these compounds as the active ingredient and methods of use of the herbicidal compositions are disclosed.

17 Claims, No Drawings

PROPIONIC ACID OXIMES

BACKGROUND OF THE INVENTION

In U.S. Pat. No. 4,200,587, 2-[p-(p-substituted phenoxy)phenoxy]propionyl oximes of the general formula

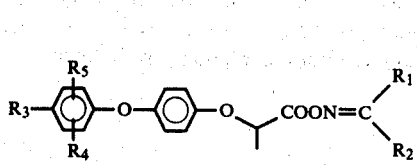

wherein $R_1$ is hydrogen, alkyl of from 1 to 6 carbon atoms or phenyl; $R_2$ is hydrogen, alkyl of from 1 to 6 carbon atoms, alkenyl of from 2 to 6 carbon atoms, alkynyl of from 2 to 6 carbon atoms or phenyl; or $R_1$ and $R_2$ together are cyclohexane which can, optionally, be monosubstituted, disubstituted or trisubstituted with alkyl of from 1 to 3 carbon atoms, $R_3$ is hydrogen, fluorine, chlorine, bromine, trifluoromethyl or nitro and $R_4$ and $R_5$ represent hydrogen or chlorine, with the proviso that $R_1$ and $R_2$ are not both hydrogen, are disclosed as herbicides.

Further, in German DOS No. 2,262,402 compounds of the general formula

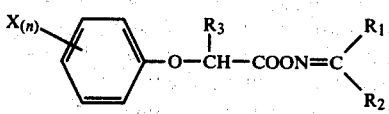

wherein $R_1$ and $R_2$ are aromatic, aliphatic, cycloaliphatic, araliphatic or heterocyclic hydrocarbon groups optionally having one or more substituents; $R_1$ can also be hydrogen; $R_1$ and $R_2$ together with the carbon atom can be nitrogen-and/or oxygen-containing cycloaliphatic hydrocarbon groups; $R_3$ is hydrogen or alkyl, X is hydrogen, alkyl, alkoxy, haloalkyl or halogen, and n is an integer from 1 to 3, are disclosed as herbicides.

SUMMARY OF THE INVENTION

This invention is directed to propionic acid oximes of the formula

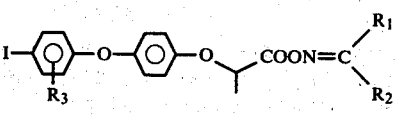

wherein $R_1$ is hydrogen, alkyl of from 1 to 6 carbon atoms or cycloalkyl of from 3 to 6 carbon atoms, $R_2$ is hydrogen, alkyl of from 1 to 6 carbon atoms, alkenyl of from 2 to 6 carbon atoms, or alkynyl of from 2 to 6 carbon atoms, or $R_1$ and $R_2$ together with the carbon atom to which they are attached form a cyclopentane or cyclohexane ring which can be mono- di- or trisubstituted with alkyl of from 1 to 3 carbon atoms, $R_3$ is hydrogen, halogen or nitro, with the proviso that $R_1$ and $R_2$ are not simultaneously hydrogen, as well as processes for their preparation. This invention is also directed to herbicidal compositions containing, as the active ingredient, a compound of formula I and methods for the use of these herbicidal compositions.

DETAILED DESCRIPTION OF THE INVENTION

The invention is directed to propionic acid oximes of the formula

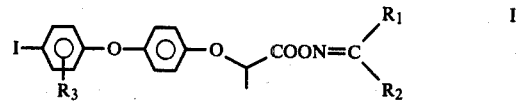

wherein $R_1$ is hydrogen, alkyl of from 1 to 6 carbon atoms or cycloalkyl of from 3 to 6 carbon atoms, $R_2$ is hydrogen, alkyl of from 1 to 6 carbon atoms, alkenyl of from 2 to 6 carbon atoms, or alkynyl of from 2 to 6 carbon atoms, or $R_1$ and $R_2$ together with the carbon atom to which they are attached form a cyclopentane or cyclohexane ring which can be mono-, di- or trisubstituted with alkyl of from 1 to 3 carbon atoms, $R_3$ is hydrogen, halogen or nitro, with the proviso that $R_1$ and $R_2$ are not simultaneously hydrogen.

This invention is also directed to processes for the preparation of the compounds of formula I as well as herbicidal compositions which contain, as the active ingredient, a compound of formula I, and methods for their use. The compounds have both preemergence and postemergence herbicidal activity.

The term alkyl encompasses both straight- and branched-chain hydrocarbon groups containing from 1 to 3 or 1 to 6 carbon atoms such as methyl, ethyl, propyl, isopropyl, butyl, isobutyl, t-butyl and the like.

The terms alkenyl and alkynyl encompass both straight- and branched-chain unsaturated hydrocarbon groups of from 2 to 6 carbon atoms such as allyl, butenyl, isobutenyl, pentenyl, isopentenyl and the like, and propargyl, butynyl, isobutynyl, pentynyl and the like.

The term halogen encompasses fluorine, chlorine, bromine and iodine and preferably chlorine and iodine.

Preferred compounds of formula I are those in which $R_1$ and $R_2$ are alkyl having 1 to 2 carbon atoms and $R_3$ is hydrogen. Compounds wherein $R_1$ and $R_2$ are methyl and $R_3$ is hydrogen or chlorine are especially preferred.

Particularly preferred compounds of formula I are:
acetone O-[2-[p-(p-iodophenoxy)phenoxy]propionyl]oxime and cyclopropyl methyl ketone O-[2-[p-(p-iodophenoxy)phenoxy]propionyl]oxime, and the D-isomers of these compounds.

Examples of other compounds of formula I are:
2-butanone O-[2-[p-(p-iodophenoxy)phenoxy]propionyl]oxime, 3-pentanone O-[2-[p-(p-iodophenoxy)phenoxy]propionyl]oxime, 3-heptanone O-[2-[p-(p-iodophenoxy)phenoxy]propionyl]oxime, (2-methyl-2-penten-4-one) O-[2-[p-(p-iodophenoxy)phenoxy]propionyl]oxime, diisopropyl ketone O-[2-[p-(p-iodophenoxy)phenoxy]propionyl]oxime, 6-undecanone O-[2-[p-(p-iodophenoxy)phenoxy]-propionyl]oxime, isopropyl ethyl ketone O-[2-[p-(p-iodophenoxy)phenoxy]propionyl]oxime, isobutyl ethyl ketone O-[2-[p-(p-iodophenoxy)phenoxy]propionyl]oxime, cyclopentanone O-[2-[p-(p-iodophenoxy)phenoxy]propionyl]oxime, cyclohexanone O-[2-[p-(p-iodophenoxy)phenoxy]propionyl]oxime, 2,4,4-trimethylcyclohexanone O-[2-[p-(p-iodophenoxy)phenoxy]propionyl]oxime and acetone O-[2-[p-(2-chloro-4-iodophenoxy)phenoxy]propionyl]oxime.

Especially preferred are the D-isomers of the compounds of formula I and consequently the D-isomers of the aforementioned individually named compounds.

The compounds of formula I are prepared by one of the procedures described below.

A. The reaction of an acid or a reactive derivative of an acid of the formula

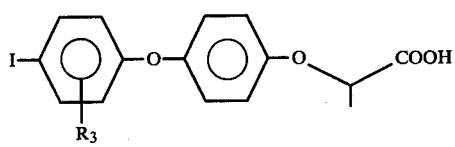

wherein $R_3$ is as previously described in formula I above, with an oxime of the general formula $$R_1R_2CNOH \qquad \text{III}$$

wherein $R_1$ and $R_2$ are as previously described in formula I. The expression "reactive derivative of an acid" refers to an acid halide or an acid anhydride.

The reaction of an acid of formula II or a reactive derivative thereof with an oxime of formula III is preferably carried out in a suitable inert solvent in the range of about $-10°$ C. to about $100°$ C. The preferred temperature range is between $20°$ C. and $70°$ C.

If a free acid of formula II is the starting material, the reaction with an oxime of formula III is carried out in the presence of dicyclohexylcarbodiimide. In carrying out this reaction the acid of formula II is dissolved in an inert organic solvent such as a chlorinated hydrocarbon, for example, dichloromethane, chloroform, carbon tetrachloride or trichloroethane, an ether, for example, diethyl ether, diisopropyl ether or dioxan, an aromatic hydrocarbon, for example benzene, toluene, xylene and the like, and then the oxime of formula III is suspended in the resulting solution. The dicyclohexylcarbodiimide is dissolved in the same solvent and the solution is added to the reaction mixture. The reaction can be carried out at a temperature between $0°$ C. and the boiling point of the reaction mixture, preferably between room temperature and $50°$ C. After about 2 hours, the reaction is complete, the reaction mixture is filtered and the filtrate is evaporated. If necessary, the residue can be purified by recrystallization or chromatography.

If an acid halide is the reactive derivative of a compound of FIG. II, the reaction with the oxime of formula III is carried out at room temperature in the presence of an acid acceptor, for example a tertiary amine such as pyridine, triethylamine and the like, or in an alkaline solution as in the Schotten-Baumann reaction. Preferred acid halides are the acid chlorides. The corresponding ester is obtained in high yields. Suitable inert solvents include benzene, toluene or petroleum ether and, in the case of the Schotten-Baumann reaction, an alkaline solution.

If an acid anhydride is the reactive derivative of a compound of FIG. II, the reaction with the oxime of formula III is carried out by heating the anhydride with the oxime in the presence of a base, preferably an alkali metal carbonate. Especially preferred is sodium carbonate.

B. The reaction of a compound of the formula

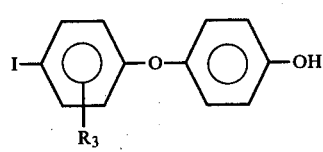

wherein Z is chlorine, bromine, iodine, mesyloxy or tosyloxy and $R_1$ and $R_2$ are as previously described in formula I above, with a compound of the formula

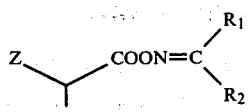

wherein $R_3$ is as previously described in formula I above, or with an alkali metal salt thereof, if necessary in the presence of a base.

A compound of formula IV is reacted with a compound of formula V or an alkali metal salt, for example sodium or potassium, of a compound of formula V by known procedures. The reaction is conveniently carried out in an inert organic solvent such as a hydrocarbon, for example benzene or toluene, an ether, for example diethyl ether, tetrahydrofuran, dimethoxyethane or the like, or hexamethylphosphoric acid triamide. Temperature and pressure are not critical. The reaction is preferably carried out at a temperature of from about $-20°$ C. to the reflux temperature of the reaction mixture, preferably between $-10°$ C. and $30°$ C.

Valuable starting materials for the preparation of the compounds of formula I are compounds of the formula

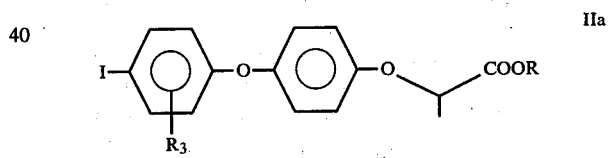

wherein R represents hydrogen or alkyl of from 1 to 6 carbon atoms and $R_3$ is hydrogen, halogen or nitro.

Formula IIa includes the acids of formula II and the corresponding $C_1$–$C_6$ alkyl esters which can be converted into the free acids by saponification.

Starting materials which are particularly preferred include 2-[p-(p-iodophenoxy)phenoxy]propionic acid and 2-[p-(p-iodophenoxy)phenoxy]propionic acid ethyl ester, 2-[p-(2-chloro-4-iodophenoxy)phenoxy]propionic acid and the ethyl ester of this acid, and particularly the D-isomers of these compounds.

The starting materials of formula IIa described above are novel compounds in the form of their D-isomers. They are also valuable as herbicides, since they have a spectrum of activity similar to the compounds of formula I. Compared to the respective racemate, these compounds have a lower phytotoxicity on cotton and soya beans.

The starting materials of formulae V and II can be prepared according to the following Reaction Scheme:

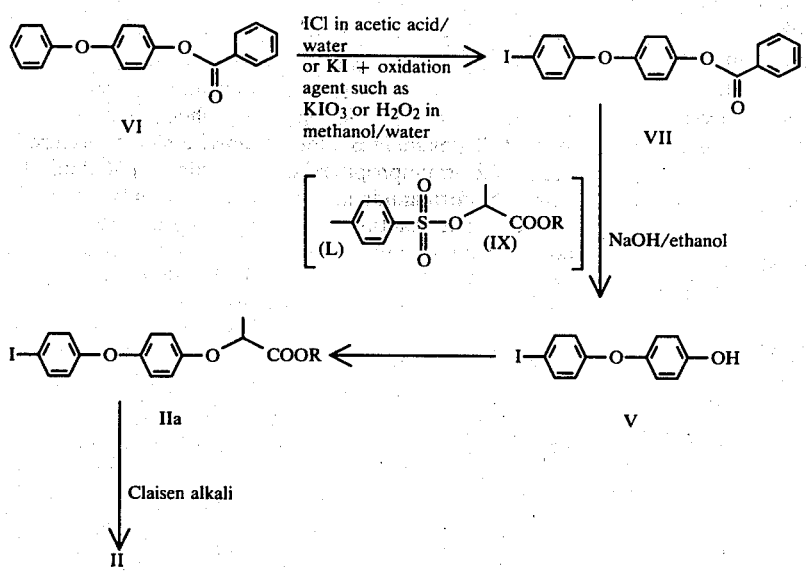

In connection with the foregoing Reaction Scheme, p-phenoxyphenyl benzoate of formula VI is either reacted with iodine monochloride in aqueous acetic acid or treated with potassium iodide and an oxidizing agent, for example potassium iodate or hydrogen peroxide, in aqueous methanol, to afford the iodo derivative of formula VII. This iodo derivative is saponified by heating in alkali, for example alcoholic sodium hydroxide, to give p-(p-iodophenoxy)phenol of formula V.

The ester of formula IIa can be prepared by reacting p-(p-iodophenoxy)phenol of formula V or a corresponding alkali metal phenolate with a lactic acid alkyl ester tolylsulfonate for example the corresponding ethyl ester, wherein R is ethyl. The ester of formula IIa, which is formed via the intermediate compound of formula IX, can be saponified to the free acid of formula II by treatment with Claisen alkali. If an optically active lactic acid alkyl ester tolylsulphonate is employed in the process, then an optically active ester of formula IIa and an optically active acid of formula II are obtained. Thus, L-(−)-lactic acid ethyl ester tolylsulphonate affords the D(+)-ethyl ester of formula IIa and the D(+)-acid of formula II.

Since the substituted propionic acid oximes of formula I have asymmetric carbon atoms in the α-position to the carbonyl group, these compounds can exist in optically active isomeric forms. In fact, these oximes can have more than one asymmetric carbon atom. The racemic compounds can be resolved in their dextrorotatory and laevorotatory isomers using known procedures as, for example, that described in Industrial and Engineering Chemistry 60(8), 12–28 (1968). The racemic mixtures as well as the isomers all have herbicidal activity with the D-isomer having the highest activity followed by the racemic mixture and the L-isomer. For example, it has been found that the D-isomer of O-[2[p(p-iodophenoxy]phenoxy]propionyl] oxime has a higher activity than the racemic mixture.

The isomers can also be manufactured by synthesis from corresponding optically active starting materials. Such starting materials are especially preferred.

In addition, and as a result of the nitrogen-carbon double bond in the oxime group

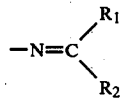

it is also possible to have in each case two geometric isomers when $R_1$ and $R_2$ are different. These isomers, the syn- and antiform, can be isolated in certain cases.

This invention is also directed to herbicidal compositions which comprise inert carrier material and, as the active ingredient, one or more compounds of formula I. These herbicidal compositions suitably contain, as the inert carrier material, at least one of the following ingredients: carrier materials, wetting agents, inert diluents and solvents.

The compounds of formula I are, in general, water-insoluble. Thus, the usual methods of formulation of insoluble materials can be followed. For example, the compounds can be dissolved in a water-immiscible solvent such as a high-boiling hydrocarbon which conveniently contains dissolved emulsifiers so that the solution acts as a self-emulsifiable oil when added to water.

The compounds of formula I can also be mixed with a wetting agent, with or without an inert diluent, to form a wettable powder which is soluble or dispersible in water. The compounds can alternatively be mixed with an inert diluent to form a solid or pulverulent product.

Suitable inert diluents are solid inert media including pulverulent or finely divided solids such as clays, sand, talc, mica, fertilizers and the like. The resulting compositions can be either dusts or materials of relatively large particle size.

Wetting agents, suitable for use with the compounds of this invention, can be anionic, cationic or nonionic.

Examples of anionic wetting agents include soaps, fatty sulfate esters such as dodecyl sodium sulfate, octadecyl sodium sulfate and cetyl sodium sulfate, fatty aromatic sulfonates such as alkylbenzene sulfonates and butylnaphthalene sulfonates, and the more complex fatty sulfonates such as the amide condensation products of oleic acid and N-methyltaurine or the sodium sulfonate of dioctyl succinate.

Examples of cationic wetting agents include cetyltrimetylammonium bromide and the like.

Examples of nonionic wetting agents include, for example, condensation products of fatty acids, fatty alcohols or fatty substituted phenols with ethylene oxides; fatty acid esters and ethers of sugars or polyhydric alcohols; condensation products of sugars or polyhydric alcohols with ethylene oxide; and block copolymers of ethylene oxide and propylene oxide.

The herbicidal compositions of this invention can also be used in aerosol form using, in addition to the propellant gas, carrier material comprising a cosolvent and a wetting agent. Suitable propellant gases include the polyhalogenated alkanes such as dichlorodifluoromethane.

The herbicidal compositions of this invention can also contain other active ingredients such as synergistic agents, insecticides, acaricides, bactericides, other herbicides, fungicides, plant growth regulators and fertilizers. Such combination preparations are suitable for increasing the activity or for broadening the spectrum of activity.

The compounds of this invention are useful as both preemergent and postemergent herbicides. They are particularly suitable in combating weeds such as slender foxtail (*Alopecurus myosuroides*) and types of millet such as cock's foot (*Echinochloa crus-gali*), great foxtail millet (*Setaria faberii*) and hairlike millet (*Panicum capillare*) in cereals. They are suitable for use against these weeds especially in cereals such as barley, oats and wheat and in rice, cotton, soya, sugar beet and vegetable crops. The compounds exhibit substantially better compatibility towards wheat and sugar beet crops than structurally similar compounds having herbicidal activity.

The premergent and postemergent herbicidal compositions of this invention are especially preferred for combating weeds in sugar beet crops. For example, acetone O-[2-[p-iodophenoxy)phenoxy]propionyl] oxime applied at a concentration of 1.25 kg/ha is sufficiently active against weeds without damaging the sugar beet crop.

In general, the compounds of this invention are effective as herbicides when applied at a concentration of about 0.3 to about 2 kg/ha with the preferred concentration range being from about 0.5 to about 1.0 kg/ha. An especially preferred application rate is about 0.8 kg/ha.

The herbicidal compositions of this invention can be in the form of concentrates suitable for storage or shipment. Such compositions can contain, e.g. from about 2% to about 90% by weight, based on the weight of the total composition, of one or more of the active compounds of this invention. These concentrates can be diluted, with the same or different inert carrier material, to concentrations which are suitable for actual use. Ready-to-use compositions can contain concentrations from about 2% to about 80% by weight of the active ingredient. Particularly preferred concentrations of active ingredients in the herbicidal compositions of this invention are from about 2% to about 8% by weight and from about 25% to about 50% by weight.

The following Examples illustrate the invention:

EXAMPLE 1 1.1 g of a 50% suspension of sodium hydride in mineral oil are washed twice with 5.0 ml portions of tetrahydrofuran under nitrogen atmosphere and then added to 15.0 ml of tetrahydrofuran. A solution of 7 g of p-(p-iodophenoxy)phenol in 30.0 ml of dimethylformamide is added dropwise to the mixture. 5.2 g of 2-bromopropionylacetone oxime in 20.0 ml of dimethylformamide are then added dropwise to the mixture. The reaction mixture is refluxed for 2 hours, cooled, poured onto ice and extracted exhaustively with ether. The ether extract is washed with water, dried over sodium sulfate and evaporated under reduced pressure. The product acetone O-[2-[p-(p-iodophenoxy)phenoxy]propionyl] oxime is purified by adsorption onto silica gel; $n_D^{20} = 1.5887$.

The starting material, p-(p-iodophenoxy)phenol, is prepared by boiling 290.4 g of p-phenoxyphenyl benzoate in 1400 ml of glacial acetic acid. To this solution is added dropwise within 10 minutes, a solution of 340 g of iodine monochloride in 800 ml of glacial acetic acid. 1800 ml of boiling water are added and the mixture is heated at 95° C. to 100° C. for 2 hours with stirring. After adding an additional 1800 ml of boiling water, the mixture is cooled to 20° C. and p-(p-iodophenoxy)phenyl benzoate crystallizes out. After adding 1000 ml of a 10% sodium hydrogen sulfite solution to the mixture, the crystal sludge is filtered under suction and rinsed with 1000 ml of dilute acetic acid and 2000 ml of deionized water. The product, p-(p-iodophenoxy)phenyl benzoate, is recrystallized from ethyl acetate/n-hexane (1:4), m.p. 121°-124° C.

300 g of p-(p-iodophenoxy)phenyl benzoate are suspended in 2800 ml of 96% ethanol, treated with 700 g of 20% sodium hydroxide solution and heated on a boiling water-bath for 90 minutes. Subsequently, the alcohol is distilled off as an azeotropic mixture and the residue is treated with 1500 ml of deionized water. After the addition of 380 ml of concentrated hydrochloric acid, the mixture is extracted three times with 1500 ml of dichloromethane each time. The dichloromethane extract is washed twice with 500 ml of saturated sodium hydrogen carbonate solution, twice with 500 ml of 2 N hydrochloric acid and twice with 500 ml of water. After drying over sodium sulphate, the solution is evaporated to 500 ml under reduced pressure and 500 ml of hot n-hexane is added to the mixture. 201 g of p-(p-iodophenoxy)phenol melting point 119° C.-121° C. is obtained.

In an analogous procedure, cyclopropyl methyl ketone O-[2-[p-(p-iodophenoxy)phenoxy]propionyl] oxime; $n_D^{20} = 1.588$, is prepared from 2-bromopropionyl cyclopropyl methyl ketone oxime and p-(p-iodophenoxy)phenol.

EXAMPLE 2

After dissolving 4 g of D-2-[p-(p-iodophenoxy)phenoxy]propionic acid and 0.76 g of acetone oxime in 40 ml of methylene chloride, a solution of 2.14 g of dicyclohexylcarbodiimide in 15 ml of methylene chloride is added dropwise at room temperature over 5 minutes. The mixture is stirred at room temperature for 1 hour and N,N'-dicyclohexylurea is separated by filtration. The filtrate is poured into water and extracted with 200 ml of methylene chloride. The extract is dried over sodium sulphate and evaporated under reduced pressure. The product, acetone O-[2-D-[p-(p-iodophenoxy)phenoxy]propionyl] oxime, yield: 73.2%;

$n_D^{20}=1.5885$; $\alpha_D=+35.44°$ (c=1.97% in chloroform) is purified by adsorption on a 10-fold amount of silica gel.

The starting material D-2-[p-(p-iodophenoxy)phenoxy]propionic acid is prepared by adding dropwise, at room temperature, a solution of 109.1 g of L-(−)-lactic acid ethyl ester totylsulfonate in 300 ml of dimethylformamide to 134.6 g of sodium p-(p-iodophenoxy)phenolate in 500 ml of dimethylformamide. The mixture is stirred for 1 hour, poured into 1000 ml of water and extracted with two 500 ml portions of ethyl acetate. The organic phase is washed with 500 ml of deionized water, dried over sodium sulfate and evaporated under reduced pressure. After crystallizing from n-hexane at −20° C., 127.1 g of D(+)-2-[p-(p-iodophenoxy)phenoxy]propionic acid ethyl ester, m.p. 48°–41° C.; $\alpha_D^{22}=16.88$(c=1.84% in chloroform) is obtained.

71.4 ml of Claisen alkali are added rapidly to 121 g D(+)-2-[p-(p-iodophenoxy)phenoxy]propionic acid in 200 ml of methanol with the temperature rising to 40° C. The mixture is stirred at room temperature for 1 hour, poured onto 1000 g of ice and acidified with 300 ml of 2 N hydrochloric acid. The reaction mixture is extracted with 1000 ml of ethyl acetate and the organic phase washed neutral with three 500 ml portions of deionized water, dried over sodium sulfate and the solvent distilled off under reduced pressure. 93.6 g of D-(+)-2-[p-(p-iodophenoxy)phenoxy]propionic acid, m.p. 121°–124° C., $\alpha_D^>=13.03$(c=1.82% in chloroform), is recrystallized from methylene chloride/n-hexane 1:2.

In an analogous procedure, cyclopropyl methyl ketone O-[2-D-[p-(p-iodophenoxy)phenoxy]propionyl]oxime; $n_D^{20}=1.5866$; $\alpha_D=+43.05$(c=1.56% in chloroform) is prepared from D-2-[p-(p-iodophenoxy)phenoxy]propionic acid and cyclopropyl methyl ketone oxime.

EXAMPLE 3

In analogous procedures as described in Examples 1 and 2, the following compounds are prepared:

2-Butanone O-[2-D-[p-(p-iodophenoxy)phenoxy]propionyl]oxime; $\alpha_D^{20}=+46.6°$; $n_D^{20}=1.5832$;

4-heptanone O-[2-D-[p-(p-iodophenoxy)phenoxy]propionyl]oxime; $\alpha_D^{22}=+50.25°$; $n_D^{20}=1.5666$;

(2-methyl-2-penten-4-one) O-[2-D-[p-(p-iodophenoxy)phenoxy]propionyl]oxime; $\alpha_D^{22}=+46.96°$; $n_D^{20}=1.5880$;

diisopropyl ketone O-[2-D-[p-(p-iodophenoxy)phenoxy]propionyl]oxime; $\alpha_D^{22}=+44.1°$; $n_D^{20}=1.5660$;

6-undecanone O-[2-D-[p-(p-iodophenoxy)phenoxy]propionyl]oxime; $\alpha_D^{22}=+48.09°$; $n_D^{20}=1.5496$;

isopropyl ethyl ketone O-[2-D-[p-(p-iodophenoxy)phenoxy]propionyl]oxime; $\alpha_D^{22}=+51.46°$; $n_D^{20}=1.5703$;

isobutyl ethyl ketone O-[2-D-[p-(p-iodophenoxy)phenoxy]propionyl]oxime; $\alpha_D^{22}=+50.64°$; $n_D^{20}=1.5652$;

cyclopentanone O-[2-D-[p-(p-iodophenoxy)phenoxy]propionyl]oxime; $\alpha_D^{22}=+46.2°$;

acetone O-[2-D-[p-(2-chloro-4-iodophenoxy)phenoxy]propionyl]oxime; $\alpha_D^{22}=+34.97°$; $n_D^{20}=1.5998$;

cyclohexanone O-[2-D-[p-(p-iodophenoxy)phenoxy]propionyl]oxime; $\alpha_D^{20}=+49.4°$; $n_D^{20}=1.5802$;

4-methyl-3-pentanone O-[2-D-[p-(p-iodophenoxy)phenoxy]propionyl]oxime; $\alpha_D^{20}=+51.46°$; $n_D^{20}=1.5703$; and 5-methyl-3-hexanone O-[2-D-[p-(p-iodophenoxy)phenoxy]propionyl]oxime; $\alpha_D^{20}=+50.65°$; $n_D^{20}=1.5652$.

EXAMPLE 4

A solution of 2.5 g of N,N-dicyclohexylcarbodiimide in 30 ml of dichloromethane is added with stirring to a mixture of 5 g D-2-[p-(2-chloro-4-iodophenoxy)phenoxy]propionic acid and 0.9 g of acetone oxime. The resulting reaction mixture is stirred for a further hour, filtered and the filter residue washed with 10 ml of ether. The residue obtained upon evaporation of the solvent is passed with hexane/ethyl acetate, 9:1, through a ten-fold amount of silica gel. There is obtained acetone O-[2-D-[p-(2-chloro-4-iodophenoxy)phenoxy]propionyl]oxime; $[\alpha]_D^{20}=+34.97°$ C. (c=1.38% in chloroform). The D-2[p-(2-chloro-4-iodophenoxy)phenoxy]propionic acid used as starting material in the above process can be obtained as follows:

A solution of 235 g of 3,4-dichloro-notrobenzene in 367 ml dimethylsulfoxide is added with stirring to a mixture of 269.5 g of hydroquinone and 90.6 g calcium-hydroxide. Stirring is continued for 6 hours at 80° C. The reaction mixture is then acidified with 800 ml of 2 n hydrochloric acid to pH=1 and then extracted three times with 800 ml ethylacetate each. The ethylacetate phase is washed with 800 ml of sodium hydrogen carbonate solution and 800 ml of water. Upon drying over sodium sulfate, the solvent is evaporated and the residue recrystallized from ethanol/water (1:1). The resulting p-(2-chloro-4-nitro-phenoxy)-phenol melts at 152° C.

110 g of the p-(2-chloro-4-nitro-phenoxy)-phenol so obtained are heated together with 9.4 of activated charcoal and 5.4 g of ferric chloride in 680 ml of methanol at reflux. 33 g of hydrazine hydrate are then added dropwise, with stirring, within 30 minutes. Stirring at reflux temperature is continued for 20 hours. The cooled reaction mixture is filtered and the solvent evaporated. The resulting residue is taken up in 400 ml of ethyl acetate, undissolved particles are removed by filtration. After addition of 400 ml of n-hexane, the product, p-(4-amino-2-chlorophenoxy)phenol, is crystallized.

A mixture of 5.4 g of iodine and 6 g of isopentylnitrite in 100 ml of acetonitrile is heated to 65° C., whereupon a solution of 10 g of p-(4-amino-2-chlorophenoxy)-phenol in 50 ml acetonitrile is added dropwise with stirring. After another 20 minutes stirring at 65° C., the reaction mixture is poured onto ice and the resulting solution is extracted three times with 200 ml of ethyl acetate, twice with 200 ml of a saturated sodium thiosulfate solution and twice with 200 ml of water. After drying over sodium sulfate, the solvent is evaporated. The residue is passed with hexane/ethyl acetate (9:1) through the ten-fold amount of silica gel.

12 g of the thus obtained p-(2-chloro-4-iodophenoxy)-phenol are dissolved in 100 ml of dimethylformamide. 0.83 g of sodium hydride are added to the resulting solution with cooling. After cessation of hydrogen evolution, a solution of L-(−)-lactic acid ethylester-tolylsulfinate in 50 ml of dimethylformamide is added dropwise with stirring and stirring is continued for 1 hour at room temperature. The reaction mixture is then poured into 500 ml of water and the resulting solution is extracted three times with 500 ml of ethyl acetate, twice with 150 ml of 2 n sodium hydroxide, and washed neutral with 600 ml of water. The residue obtained upon drying over sodium sulfate and evaporation of the solvent is passed with hexane/ethyl acetate (9:1) through a ten-fold amount of silica gel, yielding the ethyl ester of D-2-[p-(2-chloro-4-iodophenoxy)phenoxy]propionic acid. $[\alpha]_D^{20} = +15.03°$ (c=1.57% in chloroform).

8.8 g of this ester and 6 ml of Claisen alkali are heated at reflux with stirring for 1 hour, whereupon the reaction mixture is acidified, with 100 ml of 2 n hydrochloric acid to pH=1, extracted three times with 150 ml of ethyl acetate and washed neutral with 600 ml of water. The residue obtained after drying over sodium sulfate and evaporation of the solvent is passed with hexane/ethyl acetate (7:3) through a 10-fold amount of silica gel, yielding 2-D-[p-(2-chloro-4-iodophenoxy)-phenoxy]propionic acid; $[\alpha]_D^{20} = +8.89$(c=1.61% in chloroform).

EXAMPLE 5

This Example illustrates the preparation of an emulsifiable concentrate with a compound of this invention. The following ingredients are mixed:

| Ingredient | Amount |
| --- | --- |
| Compounds of formula I (e.g. product of Example 1) | 500 g |
| Condensation product of an alkyl-phenol and ethylene oxide; calcium dodecylbenzenesulfonic acid | 100 g |
| Epoxydated soya oil with an oxirane oxygen content of ca 6% | 25 g |
| Butylated hydroxytoluene | 10 g |
| Xylene | to 1 liter |

EXAMPLE 6

This Example illustrates the herbicidal activity of two of the active compounds of this invention, namely of acetone O-[2-[p-(p-iodophenoxy)phenoxy]-propionyl]oxime=Compound A and of cyclopropylmethyl ketone O-[2-[p-(p-iodophenoxy)phenoxy]propionyl]oxime=Compound B.

Compositions containing 2% of active ingredient (Compound A and Compound B, respectively) were sprayed, in dosages of 1.25 kg active ingredient per hectare, onto test plants in a greenhouse wherein a 16 hours day was simulated by use of mercury vapor lamps. The plants were evaluated for % necrosis three weeks after spraying. Necrosis is a measurement of the amount of damage to a plant; 100% necrosis corresponds to complete destruction of the plant. The results are tabulated below.

| Test plant | Percent necrosis; | |
| --- | --- | --- |
| | Compound A | Compound B |
| Echinochloa crus galli | 100 | 100 |
| Setaria faberi | 100 | 100 |
| Avena fatua | 50 | 70 |
| Alopecurus | 90 | 100 |
| myosuroides | 90 | 100 |
| Agropyron repens | 70 | 80 |
| Digitaria sanguinalis | 100 | 100 |

I claim:
1. A compound of the formula

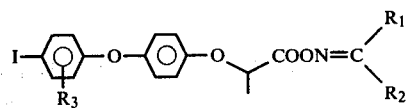

wherein $R_1$ is hydrogen, alkyl of from 1 to 6 carbon atoms or cycloalkyl of from 3 to 6 carbon atoms, $R_2$ is hydrogen, alkyl of from 1 to 6 carbon atoms, alkenyl of from 2 to 6 carbon atoms or alkynyl of from 2 to 6 carbon atoms, or $R_1$ and $R_2$ together with the carbon atom to which they are attached form a cyclopentane or cyclohexane ring which is unsubstituted or is mono-, di- or trisubstituted with alkyl of from 1 to 3 carbon atoms, $R_3$ is hydrogen, halogen or nitro with the proviso that $R_1$ and $R_2$ are not simultaneously hydrogen.

2. The compound according to claim 1, wherein $R_1$ and $R_2$ are alkyl with 1–2 carbon atoms and $R_3$ is hydrogen or chlorine.

3. The compound according to claim 1, wherein $R_1$ and $R_2$ are each methyl and $R_3$ is hydrogen or chlorine.

4. The compound according to claim 1 which is acetone O-[2-[p-(p-iodophenoxy)phenoxy]-propionyl]oxime.

5. The compound according to claim 1 which is cyclopropyl methyl ketone O-[2-[p-(p-iodophenoxy)-phenoxy]propionyl]oxime.

6. The compound of claim 1 which is acetone O-[2-[p-(2-chloro-4-iodophenoxy)phenoxy]propionyl]oxime.

7. The D-isomer of a compound according to claim 1.

8. A herbicidal composition which comprises inert carrier material and, as the active ingredient, a herbicidally effective amount of one or more of the compounds of claim 1.

9. A herbicidal composition according to claim 8 wherein the active ingredient is acetone O-[2[p-(p-iodophenoxy)phenoxy]propionyl]oxime.

10. A herbicidal composition according to claim 8 wherein the active ingredient is cyclopropyl methyl ketone O-[2-[p-(p-iodophenoxy)phenoxy]propionyl]oxime.

11. A herbicidal composition according to claim 8 wherein the active ingredient is acetone O-[2-[p-(2-chloro-4-iodophenoxy)phenoxy]propionyl]oxime.

12. A herbicidal composition according to claim 8 wherein the active ingredient is the D-isomer of the compound of claim 1.

13. A method for combating weeds which comprises applying, to the locus to be protected, a herbicidally effective amount of the composition of claim 8.

14. A method for combating weeds which comprises applying, to the locus to be protected, a herbicidally effective amount of the composition of claim 9.

15. A method for combating weeds which comprises applying, to the locus to be protected, a herbicidally effective amount of the composition of claim 10.

16. A method for combating weeds which comprises applying, to the locus to be protected, a herbicidally effective amount of the composition of claim 11.

17. A method for combating weeds which comprises applying, to the locus to be protected, a herbicidally effective amount of the composition of claim 12.

* * * * *